US011129526B2

(12) United States Patent
Ohlendorf et al.

(10) Patent No.: US 11,129,526 B2
(45) Date of Patent: Sep. 28, 2021

(54) DEVICES, METHOD, AND COMPUTER PROGRAMS FOR DETERMINING THE REFRACTION OF THE EYE

(71) Applicant: Carl Zeiss Vision International GmbH, Aalen (DE)

(72) Inventors: Arne Ohlendorf, Tübingen (DE); Alexander Leube, Tübingen (DE)

(73) Assignee: Carl Zeiss Vision International GmbH, Aalen (DE)

( * ) Notice: Subject to any disclaimer, the term of this patent is extended or adjusted under 35 U.S.C. 154(b) by 256 days.

(21) Appl. No.: 16/393,987

(22) Filed: Apr. 25, 2019

(65) Prior Publication Data

US 2019/0246891 A1    Aug. 15, 2019

Related U.S. Application Data

(63) Continuation of application No. PCT/EP2017/076580, filed on Oct. 18, 2017.

(30) Foreign Application Priority Data

Oct. 25, 2016    (DE) .......................... 102016120350.5

(51) Int. Cl.
*A61B 3/028* (2006.01)
*A61B 3/00* (2006.01)
*A61B 3/032* (2006.01)

(52) U.S. Cl.
CPC .............. *A61B 3/028* (2013.01); *A61B 3/005* (2013.01); *A61B 3/0025* (2013.01);
(Continued)

(58) Field of Classification Search
CPC ....... A61B 3/028; A61B 3/0025; A61B 3/005; A61B 3/0075; A61B 3/0041; A61B 3/032; A61B 3/0285
(Continued)

(56) References Cited

U.S. PATENT DOCUMENTS 4,432,617 A    2/1984 Itoh et al.
7,364,292 B2   4/2008 Kato
(Continued)

FOREIGN PATENT DOCUMENTS

CN    1831582 A      9/2006
CN    105611896 A    5/2016
(Continued)

OTHER PUBLICATIONS

Office action by the Indian Patent Office issued in IN 201947018572, which is a counterpart hereof, dated Mar. 24, 2021 (In Hindi and English).
(Continued)

*Primary Examiner* — Mohammed A Hasan
(74) *Attorney, Agent, or Firm* — Thrive IP®; Georg M. Hasselmann

(57) ABSTRACT

A device and computer program for determining the spherocylindrical refraction of an eye are disclosed. A component having adjustable optics is provided, the refractive power of which can be adjusted via a refractive power adjustment device. The spherocylindrical refraction is then determined from the adjustment of the refractive power adjustment device at different orientations of a typical direction of the optics or a typical direction of eye test characters.

36 Claims, 7 Drawing Sheets

(52) U.S. Cl.
CPC .......... *A61B 3/0041* (2013.01); *A61B 3/0075* (2013.01); *A61B 3/032* (2013.01); *A61B 3/0285* (2013.01)

(58) Field of Classification Search
USPC .......................................................... 351/206
See application file for complete search history.

(56) References Cited

U.S. PATENT DOCUMENTS

| | | | |
|---|---|---|---|
| 7,824,033 B2 * | 11/2010 | Lai ....................... | A61B 3/1035 351/205 |
| 9,293,513 B2 | 3/2016 | Konuma et al. | |
| 9,925,041 B2 | 3/2018 | Gerlach | |
| 10,182,717 B2 | 1/2019 | Lindig et al. | |
| 2003/0053027 A1 * | 3/2003 | Sarver ................. | A61B 3/0325 351/216 |
| 2006/0170864 A1 | 8/2006 | Kuiper et al. | |
| 2013/0188127 A1 | 7/2013 | Cabeza Guillen et al. | |
| 2015/0313463 A1 | 11/2015 | Trumm et al. | |
| 2017/0290505 A1 | 10/2017 | Correns et al. | |

FOREIGN PATENT DOCUMENTS

| | | |
|---|---|---|
| DE | 3102450 A1 | 12/1981 |
| DE | 4131799 A1 | 3/1993 |
| DE | 102013000295 A1 | 7/2014 |
| DE | 102014113682 A1 | 3/2016 |
| EP | 2606815 A1 | 6/2013 |
| WO | 2016045866 A1 | 3/2016 |

OTHER PUBLICATIONS

Internet article "Alvarez lens," and English-language machine translation thereof, available at the url: www.spektrum.de/lexikon/optik/alvarez-linse/130, last accessed May 22, 2018.

Internet article "Flüssiglinse [Liquid lens]," and English-language machine translation thereof, available at the url: de.wikipedia.org/wiki/FI%C3%BCssiglinse, last accessed May 22, 2018.

Gekeler et al.: "Measurement of astigmatism by automated infrared photoretinoscopy," Optom. Vis. Sci. Jul. 1997, vol. 74(7), pp. 472 to 482.

Ilechie et al.: "Self-refraction Accuracy with Adjustable Spectacles among Children in Ghana," Optom. Vis Sci. 92, No. 4, pp. 456 to 463, 2015.

Internet article "Phoropter," and English-language translation thereof, available at the url: de.wikipedia.org/wiki/Phoropter, last accessed Oct. 13, 2016.

Zhang et al.: "Self correction of refractive error among young people in rural China: results of cross sectional investigation," BMJ 2011;343:d4767 doi: 10.1136/bmj.d4767, Aug. 9, 2011.

Ophthalmic optics—Spectacle lenses—Vocabulary (ISO 13666:2012); German and English version EN ISO 13666:2012, Oct. 2013.

International Search Report for PCT/EP2017/076580, to which this application claims priority, dated Mar. 6, 2018.

International Preliminary Report on Patentability for PCT/EP2017/076580, to which this application claims priority, dated Feb. 22, 2019.

Office action by the Chinese Patent Office issued in CN 201780074554.8, which is a counterpart hereof, dated May 31, 2021, and English-language translation thereof.

* cited by examiner

DEVICES, METHOD, AND COMPUTER PROGRAMS FOR DETERMINING THE REFRACTION OF THE EYE

CROSS REFERENCE TO RELATED APPLICATIONS

This application is a continuation application of international application PCT/EP2017/076580, filed Oct. 18, 2017, which claims priority to German patent application DE 10 2016 120 350.5, filed on Oct. 25, 2016, both of which are hereby incorporated by reference in their entireties.

TECHNICAL FIELD

The present disclosure relates to systems for determining the refraction, i.e., light refraction, in the eye, in particular for determining the spherocylindrical refraction of the eye.

BACKGROUND

An eye may have a refractive error such as myopia (nearsightedness), hyperopia (farsightedness) or astigmatism (corneal distortion), for example. Such a refractive error is usually specified as spherocylindrical refraction with three parameters (sphere, cylinder and axis), where sphere and cylinder specify the spherical refractive power and the cylindrical refractive power, respectively, and are linked to the unit of diopter, and the axis specifies the axis position as an angle. Sphere, cylinder and axis are defined in paragraphs 11.2, 12.5 and 12.6, respectively, of the DIN EN ISO 13666:2013-10 standard and are used within this sense in this application.

In the case of refraction determination, it is possible to distinguish between subjective refraction determination and objective refraction determination. In this case, methods for subjective refraction determination are based on (subjective) feedback from a person to be examined with respect to the person's visual perception. One example in this case is a measurement based on eye charts with ever decreasing optotypes (e.g., numbers or letters) or ever decreasing symbols, in which case the person to be examined provides feedback with respect to which characters can be discerned by the person. In contrast, methods and apparatus for objective refraction determination do not require such feedback from the person to be examined with regard to the person's visual perception. The present disclosure relates to methods for subjective refraction determination.

Conventionally, the subjective refraction determination is implemented by means of a trial frame and trial lenses or a manual or digital phoropter and using optotypes, which are displayed on an external monitor. By way of example, phoropters are described at the url de.wikipedia.org/wiki/Phoropter, as of Oct. 13, 2016. Here, a person to be examined observes the optotypes and an optician or ophthalmologist inserts different trial lenses with different corrective powers into the trial frame, or changes a correction setting if a phoropter is used. The person to be examined then provides feedback in respect of what trial lenses or what settings of the phoropter allow the optotypes to be recognized to the best possible extent.

Here, the trial lenses used in the process or a corresponding correction settings of the phoropter are in each case assigned to a certain refractive error, which is corrected by the respective trial lens or the setting of the phoropter. Here, the subjective refraction determination explained above can be implemented separately for each eye (in monocular fashion) or else for both eyes together (in binocular fashion).

The above-described procedure is substantially stationary; i.e., it is bound to the premises of the optician or ophthalmologist and requires an appropriately schooled optician or ophthalmologist to carry out the refraction determination. However, since opticians or ophthalmologists are in short supply in some areas, it may be the case that there is insufficient infrastructure present, i.e., there are insufficient numbers of opticians or ophthalmologists with appropriate equipment, to measure refractive errors regionwide and adequately correct these where necessary, for example by prescribing spectacles.

Previous mobile solutions, which in part make use of objective refraction methods such as eccentric photorefraction, have numerous disadvantages since there is a need either for relatively expensive specialist equipment and/or for trained staff.

Moreover, a simplified procedure is applied in order to carry out an approximate measurement of the refractive error over broad levels of the population. Simple adjustable spectacle lenses are used to this end. Corresponding studies are published, for example, in Mingzhi Zhang et al., BMJ 2011, August 2011, or in Ilechie AA. et al., Optom. Vis. Sci. 2015, April.

However, in the methods described there, it is only the so-called spherical equivalent of the refractive error that is determined, i.e., a single parameter. Although this facilitates a certain correction of visual defects and/or statistical examinations, it is less accurate than a determination of the three separate parameters for spherical refractive power, cylindrical refractive power and axis position. On the other hand, these methods are carried out by the persons to be examined themselves and require no trained staff and only relatively simple technical means, facilitating examinations covering comparatively large areas.

US 2006/0170864 A1 has disclosed an apparatus with two different orientations of the typical direction of optotypes for testing the refractive error of a patient, the apparatus comprising a variable lens and means for controlling the refractive behavior of the variable lens.

DE 10 2013 000 295 A1 has disclosed a method and apparatus for stimulating the accommodation of at least one eye of a subject, which facilitates an option for determining a set of ophthalmological data of at least one eye of the subject and, in particular, for measuring the refractive error of the subject and for ascertaining a corresponding optical correction and which, in particular, comprises an apparatus for objective refraction determination.

US 2003/0053027 A1 discloses a computer program for controlling an apparatus including an optical unit having an adjustable refractive power and a method for refraction determination.

DE 41 31 799 A1 discloses a method, optotypes and an apparatus for carrying out a computer-assisted subjective refraction determination. According to the method, a computer provides an object, a test image and decision alternatives, which typically have directional orientation, for the person to be examined. The person to be examined selects a decision alternative by means of a control element and the computer makes a decision as to what lenses, filters and/or the like should be placed in front of the eye or what adjustments should be undertaken, with these steps being repeated until optical symmetry is achieved for the person to be examined.

WO 2016/045866 A1 has disclosed a display apparatus for demonstrating optical properties of spectacle lenses. A holding apparatus holds a first optical system for refraction determination which is designed to determine the subjective refraction of the first eye when the holding apparatus is placed on the head of the user and/or the first optical imaging system is designed to be modifiable.

SUMMARY

It is an object of the present application to provide an apparatus, a method and a computer program which facilitate a faster and easier calculation of the spherocylindrical properties of the eye.

In a first aspect of the disclosure, a system having an optical unit having an adjustable refractive power, a method for ascertaining a spherocylindrical refraction of an eye of a user, and a computer program for carrying out the method are provided for this purpose. Further exemplary embodiments are described below.

By means of the apparatus described in US 2006/0170864 A1, it is possible to ascertain the spherocylindrical refraction of the eye by trial and error in a system with many degrees of freedom, depending on the skill of the person carrying out the measurement.

Proceeding from US 2006/0170864 A1, it is a second object of the present disclosure to provide an improved option in the form of an apparatus, method and computer program in order to ascertain the spherocylindrical refraction of the eye within a short period of time, as independently as possible from the skill of the person carrying out adjustments.

In a second aspect of the disclosure, a system having an optical unit having an adjustable refractive power, a method for ascertaining a spherocylindrical refraction of an eye of a user, and a computer program for carrying out the method are provided for this purpose. Additional exemplary embodiments are discussed below.

In addition to the above-described properties, US 2006/0170864 A1 does not teach how an apparatus can be advantageously configured in order to assist a targeted ascertainment of the spherocylindrical refraction of the eye.

Proceeding from US 2006/0170864 A1, it is therefore a third object of the present disclosure to provide an improved option in the form of an apparatus and a method in order to improve the targeted adjustment for ascertaining the spherocylindrical refraction such that it the complexity of the adjustment options for the person using this is reduced.

In a third aspect of the disclosure, a system having an optical unit having an adjustable refractive power and a method or ascertaining a spherocylindrical refraction of an eye of a user, are provided for this purpose. Further exemplary embodiments are discussed below.

The procedure disclosed in US 2003/0053027 A1 may be problematic for persons with a pronounced cylinder. This likewise applies to the option disclosed in US 2006/0170864 A1.

Proceeding from US 2003/0053027 A1, it is therefore a fourth object of the present disclosure to provide an improved option in the form of an apparatus, method and computer program in order to reliably ascertain the spherocylindrical refraction of the eye for persons with a pronounced cylinder.

Proceeding from US 2006/0170864 A1, it is therefore a fifth object of the present disclosure to provide an improved option in the form of an apparatus, method and computer program in order to reliably ascertain the spherocylindrical refraction of the eye for persons with a pronounced cylinder.

In a fourth aspect of the disclosure, a system a having precisely two different orientations of the typical direction of optotypes, a method of measuring the orientation of the typical direction of the refractive power, and a computer program for carrying out the method are provided for this purpose. Dependent claims of the fourth aspect of the disclosure define further exemplary embodiments.

In a fifth aspect of the disclosure, a system optical unit with an adjustable refractive power, which has a typical direction of the refractive power, a method for ascertaining a spherocylindrical refraction of an eye of a user including displaying optotypes with three different orientations of a typical direction of the optotypes and a computer program for carrying out the method are provided for this purpose. Further exemplary embodiments are discussed below.

The first aspect of the disclosure provides a system comprising:
  an optical unit (13; 20) with an adjustable refractive power,
  a refractive power setting device (14; 22) for setting the refractive power of the optical unit (13; 20) in accordance with a setting value,
  a computer program with a program code which, when executed on a computing device (11), causes:
  optotypes (71A-C) that are observable through the optical unit (13; 20) to be displayed on a display (12; 70),
  a first value, which specifies a spherical refractive power, a second value, which specifies a cylindrical refractive power, and a third value, which specifies an axis position of the cylindrical refractive power, to be calculated
  on the basis of three setting values of the refractive power setting device (14; 22) at three different orientations of the typical direction (52) of the optotypes (71A-C).

The system is characterized in that the three different orientations of the typical direction (52) of the optotypes (71A-C) have an angular distance of between 55° and 65° from one another.

Moreover, in the first aspect of the disclosure, a method is provided for ascertaining the spherocylindrical refraction of an eye of a user, comprising:—displaying optotypes (71A-C) with three different orientations of a typical direction (52) of the optotypes (71A-C),
  ascertaining respective setting values of an optical unit with an adjustable refractive power at the three different orientations of the typical direction (52) of the optotypes (71A-C),
  calculating a first value, which specifies a spherical refractive power, a second value, which specifies a cylindrical refractive power, and a third value, which specifies an axis position of the cylindrical refractive power, on the basis of the respective setting values.

The method is characterized in that the three different orientations of the typical direction (52) of the optotypes (71A-C) have an angular distance of between 55° and 65° from one another.

Moreover, a computer program with a program code is provided in the first aspect of the disclosure, the program code, when executed on a processor, causing the method according to the method of the first aspect of the disclosure to be carried out.

When the system is used by a user as intended, the first value, the second value and the third value specify the spherocylindrical refraction (sphere, cylinder and axis) of an eye of the user within the scope of the measurement accuracy of the system. Thus, a user can be provided with an option for independently determining the spherocylindrical refraction of their eye or their eyes by way of relatively simple means. Here, use as intended means, in particular, that the user uses the system according to instructions. Here, use as intended contains the user peering through the optical unit onto optotypes or other elements such as articles, for example, by means of an eye to be examined and the user setting a setting value for the refractive power of the optical unit at which the sharpest visual impression is present by means of the refractive power setting device.

To this end, in a typical exemplary embodiment, the program code, when executed on the computing device, can cause the computing device to output instructions to the user according to the intended use. This makes operating the system easier for the user.

Optotypes should be understood to mean signs that the person to be examined can observe through the optical unit. Various optotypes can be used, for example standardized optotypes (Landolt rings, E charts, possibly with further optotypes such as letters or numbers, for example, connected thereto), natural images, sinusoidal gratings with different spatial frequencies at the same or with varying contrast, numbers, letters or symbols. Here, optotypes are typically displayed in different sizes.

In a typical exemplary embodiment, the program code, when executed on the computing device, causes optotypes that are observable through the optical unit to be displayed on a display. In this way, the optotypes are not required as separate component. However, they may also be provided as a separate component, e.g., in printed form. When the apparatus is used as intended, the user then observes the optotypes through the optical unit with the eye to be examined and the user sets the setting value in such a way that they see the optotypes as sharply as possible.

The refractive power should be understood to mean the reciprocal of the focal length, as is conventional in optics. The refractive power is usually used in diopters as legal unit of refractive power of optical systems in the states in the EU.

In general, a computing device is a device which can carry out calculations (e.g., calculations explained in more detail below) in order to calculate the first, second and third value from the at least two setting values. Typically, such a computing device comprises at least one microprocessor and a memory, in which a corresponding program is saved. By way of example, a computer, a smartphone or a tablet PC can be used as computing device. By virtue of a computer program being provided, a user can, in particular, use their own computing device (e.g., their own computer). The system may also comprise the computing device in other exemplary embodiments.

The second aspect of the disclosure provides a system comprising:

an optical unit (13; 20) with an adjustable refractive power, wherein the optical unit (13; 20) has a typical direction (25) of the refractive power, an orientation setting device (28) for setting an orientation of the typical direction (25) of the refractive power, a refractive power setting device (14; 22) for setting the refractive power of the optical unit (13; 20) in accordance with a setting value, characterized in that the system comprises a computer program with a program code which, when executed on a computing device (11), causes a first value, which specifies a spherical refractive power, a second value, which specifies a cylindrical refractive power, and a third value, which specifies an axis position of the cylindrical refractive power, to be calculated on the basis of at least two setting values of the refractive power setting device (14; 22) at different orientations of the typical direction (25) of the refractive power.

Moreover, in the second aspect of the disclosure, a method is provided for ascertaining the spherocylindrical refraction of an eye of the user, comprising:

ascertaining at least two setting values by setting a refractive power of an optical unit with a typical direction of the refractive power, characterized in that there is a calculation of a first value, which specifies a spherical refractive power, a second value, which specifies a cylindrical refractive power, and a third value, which specifies an axis position of the cylindrical refractive power, on the basis of the at least two setting values of the refractive power setting device at different orientations of the typical direction (25) of the refractive power.

Moreover, a computer program with a program code is provided in the second aspect of the disclosure, the program code, when executed on a processor, causing the method according to the method of the second aspect of the disclosure to be carried out.

According to the second, third and fifth aspect of the disclosure, the optical unit has a typical direction of the refractive power and the system further comprises an orientation setting device for setting an orientation of the typical direction of the refractive power of the optical unit. The refractive power of the optical unit has a typical direction if the refractive power of the optical unit is not rotationally symmetric, in particular if the refractive power of the optical unit has a cylindrical component that differs from zero. In particular, this can be achieved by a non-rotationally-symmetric configuration of the optical unit.

When used as intended according to the second, third and fifth aspect of the disclosure, the at least two setting values are then set at different orientations of the typical direction of the refractive power of the optical unit. In this way, the eye to be examined is measured along different directions. Then, the first, second and third value can be calculated by combining these measurements.

By way of example, the orientation setting device may comprise a frame in which the optical unit is mounted in rotatable fashion. Then, the different orientations can be set by manual or motor-driven rotation of the optical unit. Here, the orientation setting device may have markings and/or latching positions for the optical unit in order to make it easier for the user to set the orientations.

Typically, the orientation setting device comprises an alignment sensor for measuring the orientation of the typical direction of the refractive power. By way of example, such alignment sensors are also installed in smartphones and are commercially available. In this way, the orientation can be captured automatically and then transmitted to the computing device. In this way, the actual orientation of the typical direction of the refractive power can be taken into account by the computing device when calculating the first, second and third value, and so the calculation becomes independent of the accuracy with which the user sets the orientation.

The typical direction of the refractive power of the optical unit can be defined by an axis position of a cylindrical refractive power of the optical unit, wherein the refractive power setting device may be configured to set a spherical refractive power of the optical unit according to the setting value. Such an optical unit with a fixed cylindrical refractive power and an adjustable spherical refractive power is realizable in a relatively cost-effective manner since it is only the spherical refractive power that has to be adjusted.

In such an exemplary embodiment, the program code, when executed on the computing device, can cause the computing device to output an information item to the user that the refractive power of their eye has no measurable cylindrical refractive power if the setting values at the various orientations of the typical direction of the refractive power are the same. In this case, the user may moreover be invited to carry out setting the refractive power of the optical unit again with an adjusted cylindrical refractive power of the optical unit for the purposes of determining the spherical refractive power of their eye and/or to determine the spherical refractive power of their eye by means of a further optical unit, which has no cylindrical refractive power but an adjustable spherical refractive power.

In such a case, where the eye has no cylindrical refractive power, it is not possible to accurately determine the spherical refractive power of the examined eye with the procedure that uses an optical unit with a fixed cylindrical refractive power and adjustable spherical refractive power with different orientations of the typical direction. The spherical refractive power of the eye can then be determined by the aforementioned additional setting or determination, to which the user is invited in this case.

The third aspect of the disclosure provides a system comprising:

an optical unit (13; 20) with an adjustable refractive power and an adjustable typical direction (25) of the refractive power, wherein the typical direction (25) of the refractive power of the optical unit (13; 20) is defined by an axis position of a cylindrical refractive power of the optical unit (13; 20), a refractive power setting device (14; 22) for setting the spherical refractive power of the optical unit (13; 20) in accordance with a setting value, an orientation setting device (28) for setting an orientation of the typical direction (25) of the refractive power, wherein the system is configured to determine a first value, which specifies a spherical refractive power, a second value, which specifies a cylindrical refractive power, and a third value, which specifies an axis position of the cylindrical refractive power, on the basis of setting values of the refractive power setting device and settings of the orientation of the typical direction of the refractive power, characterized in that the cylindrical refractive power of the optical unit (13; 20) lies between 0.25 dpt and 0.5 dpt and in that the system comprises a computer program with a program code which, when executed on a computing device (11), causes the first value, the second value and the third value to be calculated on the basis of at least two setting values.

Moreover, in the third aspect of the disclosure, a method is provided for ascertaining the spherocylindrical refraction of an eye of the user, comprising:

ascertaining at least two setting values by setting a refractive power of an optical unit with a typical direction of the refractive power, and calculating a first value, which specifies a spherical refractive power, a second value, which specifies a cylindrical refractive power, and a third value, which specifies an axis position of the cylindrical refractive power, on the basis of the at least two setting values, characterized in that the cylindrical refractive power of the optical unit (13; 20) lies between 0.25 dpt and 0.5 dpt.

Moreover, a computer program with a program code is provided in the third aspect of the disclosure, the program code, when executed on a processor, causing the method according to the method of the third aspect of the disclosure to be carried out.

Typically, the cylindrical refractive power of the optical unit lies between 0.25 dpt and 0.5 dpt, particularly in a third aspect of the disclosure, albeit not restricted to this aspect of the disclosure only. In the case of a cylindrical refractive power below approximately 0.25 dpt, the cylindrical effect is practically not perceivable by the eye to be examined; this may lead to incorrect measurements. In the case of a cylindrical refractive power of more than 0.25 dpt, the rotational symmetry of the refractive power is sufficiently broken and the optical unit consequently has a typical direction, as a result of which the above-described measurements with various orientations of the typical direction are made possible. If the cylindrical refractive power of the optical unit is below approximately 0.5 dpt, it can be neglected when calculating the first, second and third value, simplifying the calculation.

According to the first and fourth aspect of the disclosure, the optotypes have a typical direction, i.e., no rotational symmetry, wherein the program code, when executed on the computing device, causes the optotypes to be displayed successively in time with different orientations of the typical direction. In particular, optotypes have a typical direction when they are not rotationally symmetric. In the case of conventional optotypes, in which the characters are presented in rows, with the optotypes becoming smaller from row to row, the row direction corresponds to the typical direction. In the case of Landolt rings as optotypes, the typical direction is defined by the cutouts of the otherwise rotationally symmetric rings. Expressed differently, the cutout in this case breaks the rotational symmetry otherwise present.

The use of optotypes in which the orientation of the typical direction is adjusted represents an alternative procedure to the use of an optical unit with a typical direction of the refractive power, the orientation of which is adjustable. The eye can also be measured in different directions by changing the orientation of the optotypes, and the first, second and third value can be determined by combining the measurements.

According to the explanations above, the program code can be configured in such a way that, when executed on the computing device, the computing device calculates the first value, the second value and the third value on the basis of the at least two setting values at different orientations of the typical direction of the refractive power and/or at different orientations of the typical direction of the optotypes. In this context, the program code being configured in such a way means that, when used as intended, i.e., if the user correctly determines the setting values at the different orientations of the typical direction of the refractive power and/or at different orientations of the typical direction of the optotypes, the calculation of the first, second and third value carried out by means of the program code on the computing device yields sphere, cylinder and axis of the examined eye within the scope of the measurement accuracy of the system.

In one exemplary embodiment, the at least two setting values at different orientations of the typical direction of the refractive power and/or at different orientations of the typical direction of the optotypes comprise three setting values at three different orientations of the typical direction of the refractive power and/or at three different orientations of the typical direction of the optotypes, i.e., the program code is designed for a corresponding calculation. Thus, when the apparatus is used as intended, the eye is measured in three directions and the first, second and third value can be calculated from the corresponding three setting values. Typically, the three different orientations of the typical direction of the refractive power and/or the three different orientations of the typical direction of the optotypes have an angular distance of approximately 60°, for example, between 55° and 65°, from one another, simplifying the calculation. Other angular distances between the orientations can also be used in other exemplary embodiments, in particular angles of less than 60° as well. In the first aspect of the disclosure, this is realized for the typical direction of the optotypes.

Here, the first, second and third value is calculated in a manner known per se. By way of example, more details in respect of these calculations can be gathered from Gekeler F, Schaeffel F, Howland H C, Wattam-Bell J. Measurement of astigmatism by automated infrared photoretinoscopy. Optom. Vis Sci [Internet]. 1997; 74:472-82, retrievable from the url www.ncbi.nlm.nih.gov/pubmed/9293513.

The fourth aspect of the disclosure provides a system comprising:

an optical unit (13; 20) with an adjustable refractive power, a refractive power setting device (14; 22) for setting the refractive power of the optical unit (13; 20) in accordance with a setting value, a computer program with a program code which, when executed on a computing device (11), causes optotypes (71A-C) that are observable through the optical unit (13; 20) to be displayed on a display (12; 70), and in that a first value, which specifies a spherical refractive power, a second value, which specifies a cylindrical refractive power, and a third value, which specifies an axis position of the cylindrical refractive power, are calculated on the basis of setting values of the refractive power setting device (14; 22) at different orientations of the typical direction (52) of the optotypes (71A-C), characterized in that the calculation is implemented on the basis of two setting values at two different orientations of the typical direction (52) of the optotypes (71A-C) and on the basis of an information item about an axis position of an eye.

Moreover, in the fourth aspect of the disclosure, a method is provided for ascertaining the spherocylindrical refraction of an eye of a user, comprising:

displaying optotypes (71A-C) at different orientations of a typical direction (52) of the optotypes (71A-C), ascertaining respective setting values of an optical unit with an adjustable refractive power at the different orientations of the typical direction (52) of the optotypes (71A-C), calculating a first value, which specifies a spherical refractive power, a second value, which specifies a cylindrical refractive power, and a third value, which specifies an axis position of the cylindrical refractive power, on the basis of setting values at different orientations of the typical direction, characterized in that the calculation is implemented on the basis of two setting values at two different orientations of the optotypes and an information item about an axis position of an eye.

Moreover, a computer program with a program code is provided in the fourth aspect of the disclosure, the program code, when executed on a processor, causing the method according to the method of the fourth aspect of the disclosure to be carried out.

The fifth aspect of the disclosure provides a system comprising:

an optical unit (13; 20) with an adjustable refractive power, which has a typical direction (25) of the refractive power, a refractive power setting device (14; 22) for setting the refractive power of the optical unit (13; 20) in accordance with a setting value, an orientation setting device (28) for setting an orientation of the typical direction (25) of the refractive power, wherein the system is configured to determine a first value, which specifies a spherical refractive power, a second value, which specifies a cylindrical refractive power, and a third value, which specifies an axis position of the cylindrical refractive power, on the basis of setting values of the refractive power setting device and settings of the orientation of the typical direction of the refractive power, characterized in that the system comprises a computer program with a program code which, when executed on a computing device (11), causes the first value, the second value and the third value to be calculated on the basis of two setting values of the refractive power setting device (14; 22) at two different orientations of the typical direction (25) of the refractive power and on the basis of an information item about an axis position of an eye.

Moreover, in the fifth aspect of the disclosure, a method is provided for ascertaining the spherocylindrical refraction of an eye of a user, comprising:

ascertaining at least two setting values of a refractive power of an optical unit with a typical direction of the refractive power at different orientations of the typical direction of the refractive power, and calculating a first value, which specifies a spherical refractive power, a second value, which specifies a cylindrical refractive power, and a third value, which specifies an axis position of the cylindrical refractive power, on the basis of the at least two setting values, characterized in that the calculation is implemented on the basis of two setting values at two different orientations of the typical direction of the refractive power and an information item about an axis position of an eye.

Moreover, a computer program with a program code is provided in the fifth aspect of the disclosure, the program code, when executed on a processor, causing the method according to the method of the fifth aspect of the disclosure to be carried out.

Alternatively, the at least two setting values at different orientations of the typical direction of the refractive power, for example in the fifth aspect of the disclosure, and/or at different orientations of the typical direction of the optotypes, e.g., in the fourth aspect of the disclosure, may comprise two setting values at two different orientations of the typical direction of the refractive power and/or of the typical direction of the optotypes, wherein the program code is configured in such a way that, when executed on the computing device, the computing device calculates the first value, the second value and the third value on the basis of the two setting values and on the basis of an information item about an axis position and/or an information item about the two different orientations of the typical direction of the refractive power and/or the two different orientations of the typical direction of the optotypes. In such a case, the axis position of the examined eye is ascertained in the case of intended use and the information item about the axis position of the axis of the eye is provided, the latter then corresponding to the third value, such that then only setting values for two different orientations are required to calculate the first and second value. For persons with a more pronounced astigmatism, this procedure has a greater accuracy than the procedure with three different orientations of the typical direction of the refractive power and/or with three different orientations of the typical direction of the optotypes.

To this end, the program code, when executed on the computing device, can cause a dial that is observable through the optical unit to be displayed on a display. If used as intended, the user can then ascertain the axis position of the examined eye with the aid of the dial by virtue of determining which direction of the dial appears sharpest. In this way, it is possible to provide the information item about the axis position.

Here, the two different orientations of the typical direction of the refractive power and/or of the optotypes typically correspond to the axis position and a direction approximately perpendicular thereto (e.g., at an angle of between 85° and 95°), corresponding to a measurement along the two principal meridians of the eye. This simplifies the calculation of the first and the second value. Here, the principal meridians are the axes of the eye that have a maximum or minimum refractive power. In this case, the information item about the axis position simultaneously represents an information item about the two different orientations of the typical direction of the refractive power and/or of the optotypes.

It should be noted that more than two or three orientations of the typical direction can also be used. In this case, more setting values are obtained than are required for determining the first, second and third value. With the aid of conventional methods of error analysis, this can be used to reduce statistical measurement errors, which are caused by inaccurate setting of the setting values.

In a typical exemplary embodiment, the adjustable optical unit may comprise an Alvarez lens. Here, an Alvarez lens comprises two lens elements which are displaceable in relation to one another in one direction in order to modify the refractive power of the Alvarez lens. By way of example, a description of such an Alvarez lens is found at the url www.spektrum.de/lexikon/optik/alvarez-linse/130, as of Aug. 26, 2016. Thus, in particular, the spherical refractive power of the Alvarez lens can be modified by displacing the lens elements in relation to one another. Moreover, cheap Alvarez lenses usually have a cylindrical refractive power and consequently have a typical direction. In the case of an Alvarez lens, the refractive power setting device may comprise a setscrew. In this way, the optical unit with the refractive power setting device is implementable in a cost-effective manner.

In another exemplary embodiment, the adjustable optical unit comprises an optically modifiable liquid lens. Here, a liquid crystal layer, for example, may be provided between glass plates like a liquid crystal display, where molecules of the liquid crystal layer can be arranged differently by way of an applied voltage, for example in such a way that, from a center point, they are concentrated more strongly to the outside in radial fashion. Consequently, the refractive power can be changed in such liquid crystal arrangements by applying a voltage. By way of example, such liquid lenses are described at the url de.wikipedia.org/wiki/Fl%C3%BCssiglinse. The refractive power of such a liquid lens may be radially symmetric without typical direction, particularly when using optotypes with a changeable orientation of the typical direction.

Typically, the refractive power setting device comprises an interface for transmitting the setting values to the computing device. Thus, the user need not transfer the setting values by hand. Here, the interface can be a wired interface, for example a USB interface, or a wireless interface such as a Bluetooth interface or a Wi-Fi interface.

Here, the system can be configured as a head-mounted apparatus, wherein the head-mounted apparatus comprises the computing device or a receptacle for the computing device. Hence, a compact appliance is provided to the user and correct positioning on the head can be ensured as a result of the mountability on the head. If the receptacle is provided, the computing device can be a smartphone or tablet, in particular.

By way of example, the head-mounted apparatus can have a form similar to smartglasses or VR glasses. In the case of smartglasses, the surroundings can also be perceived visually in addition to the presented optotypes, while a visual perception is only implemented via a respective display in the case of virtual-reality glasses. The smartglasses or virtual-reality glasses may also provide further functions to the user, for example perimetry measurements as described in the German patent application DE 10 2014 113 682.

The head-mounted apparatus may also have the form of a spectacle frame, in which the optical unit is installed. This may also ensure correct positioning of the optical unit.

BRIEF DESCRIPTION OF THE DRAWINGS

The disclosure will now be described with reference to the drawings wherein.

DESCRIPTION OF EXEMPLARY EMBODIMENTS

Figure 1:
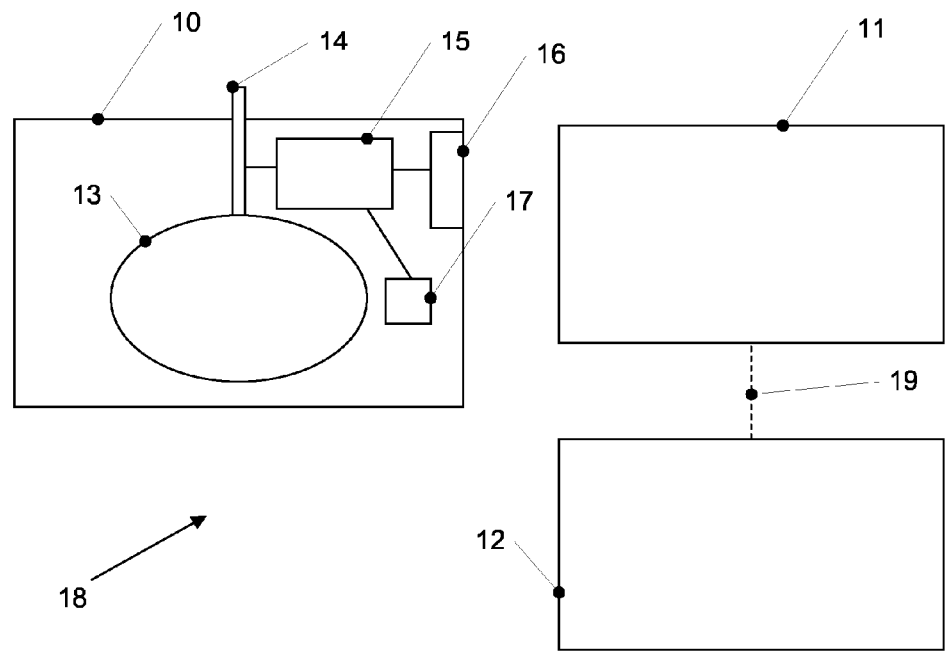
FIG. 1 shows a block diagram of an apparatus in accordance with one exemplary embodiment.

FIG. 1 schematically illustrates a block diagram of a system 18 according to one exemplary embodiment. The system 18 of FIG. 1 comprises a component 10, a computing device 11 and a device 12 for displaying optotypes.

The component 10 has an optical unit 13, which is adjustable in terms of its refractive power by means of a refractive power setting device 14. If the optical unit 13 is movable, e.g., rotatable, in the component 10, the component 10 comprises an alignment sensor 17 for determining an orientation of the optical unit 13.

The device 12 for illustrating optotypes can be a conventional eye chart, on which optotypes (letters, numbers and/or symbols) are printed in various sizes. Alternatively, the device 12 may comprise a display which, as indicated in FIG. 1 by a dashed line 19, is actuated by the computing device 11 in order to display optotypes. When used as intended, a user looks at the optotypes of the device 12 through the optical unit 13 with an eye to be examined and sets the optical unit 13 to a refractive power at which the optotypes are the most in focus by means of the refractive power setting device 14. In the exemplary embodiment of FIG. 1, the corresponding setting value of the refractive power setting device 14 is stored in a memory 15 and then transmitted to the computing device 11 via an interface 16.

The computing device 11 receives setting values stored in the memory 15 via the interface 16 and calculates the refraction of the eye to be examined as spherocylindrical refraction (sphere, cylinder and axis), i.e., as values for the spherical and cylindrical refractive power and the axis position, therefrom. Various procedures to this end are explained in more detail with reference to FIGS. 4-9.

Figure 2A:
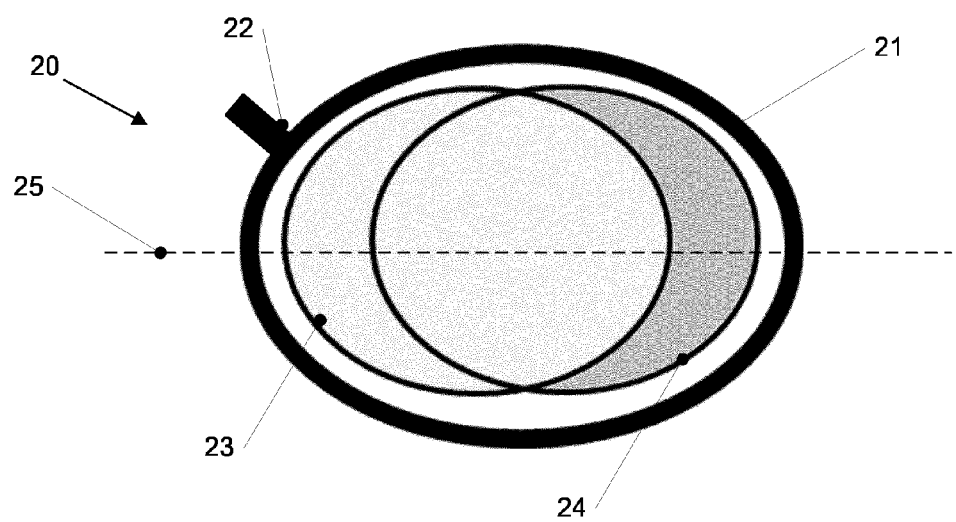
FIGS. 2A and 2B show illustrations of an adjustable optical unit according to one exemplary embodiment.
Figure 2B:
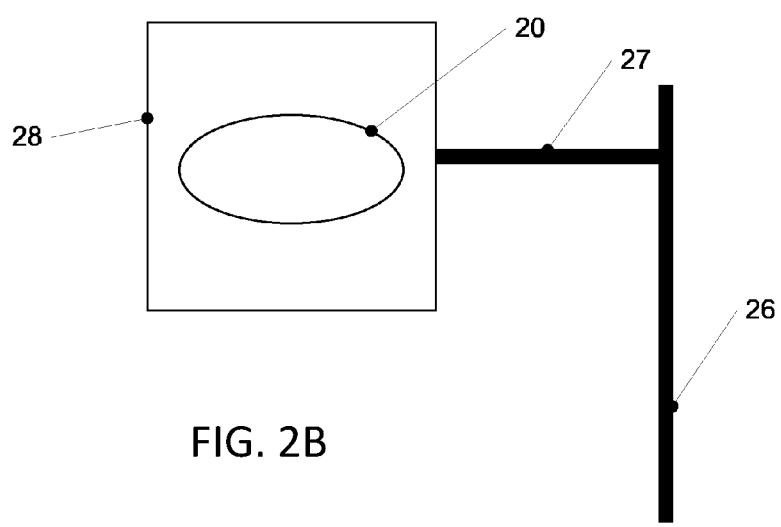

FIGS. 2A and 2B show details of possible implementations of the optical unit 13. FIG. 2A shows an example of an optical unit with an adjustable refractive power, an Alvarez lens 20. To this end, the Alvarez lens 20 of FIG. 2A comprises, in particular, a first lens element 23 and a second lens element 24, which are arranged in a plastic frame 21. By virtue of rotating a setscrew 22, which represents an example of a refractive power setting device, the first lens element 23 and the second lens element 24 are movable relative to one another along an axis 25 in order thus to change the spherical refractive power of the Alvarez lens 20. Here, the Alvarez lens 20 has a fixed cylindrical refractive power, which is produced by production-related tolerances, for example, and which typically has a value of between 0.25 dpt and 0.5 dpt. Hence, the refractive power of the Alvarez lens is not rotationally symmetric. Consequently, the Alvarez lens 20 has a typical direction. For the following explanations, the assumption is made that the typical direction corresponds to the axis 25.

As illustrated in FIG. 2B, the Alvarez lens 20 has a rotatable arrangement in a frame 28 in one exemplary embodiment, wherein the frame 28 is fastenable to a stationary object, for example a table, via a linkage 26, 27. As a result of the rotatable arrangement of the Alvarez lens 20 in the frame 28, it is possible to precisely set a direction of the axis 25, and hence an orientation of the typical direction of the Alvarez lens 20. To this end, an angle scale is typically available on the frame 28, by means of which angle scale the axis 25 is adjustable to a certain angle. Moreover, the frame 28 typically offers latching positions that are spaced apart by 60° or 90° in order to be able to carry out measurements as described below.

In a certain exemplary embodiment, the components discussed with reference to FIGS. 1 and 2, i.e., the system 18, may be arranged in a head-mounted apparatus 30 in the style of virtual-reality glasses, as illustrated schematically in FIG. 3. As a result of this, a compact arrangement for refraction determination is provided, and correct positioning of the system relative to the eyes of the user is simplified. In particular, the element 12 can be implemented as displays for both eyes and a component 10 is provided for both eyes in the case of such a head-mounted apparatus 30. The computing device 11 may likewise be integrated in the head-mounted apparatus 30. Alternatively, the computing device 11 and the element 12 may also be realized in the form of a smartphone or tablet, with the element 12 then being formed by the display of the smartphone or tablet. Then, the smartphone or tablet is inserted in a holder in the head-mounted apparatus 30.

Figure 3:
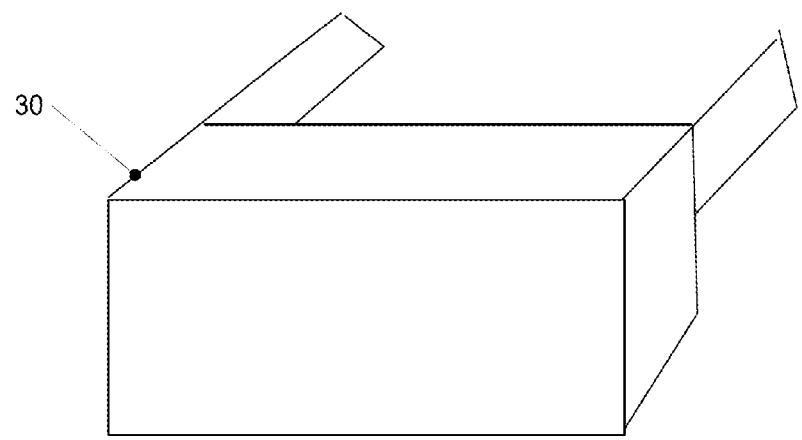
FIG. 3 shows a schematic illustration of a head-mounted apparatus according to one exemplary embodiment.

Next, different procedures for determining the spherocylindrical refraction by means of the apparatuses explained with reference to FIGS. 1-3 are illustrated with reference to FIGS. 4-9. The methods described below can be implemented, in particular, with the aid of a computer program that runs on the computing device 11.

Figure 4:
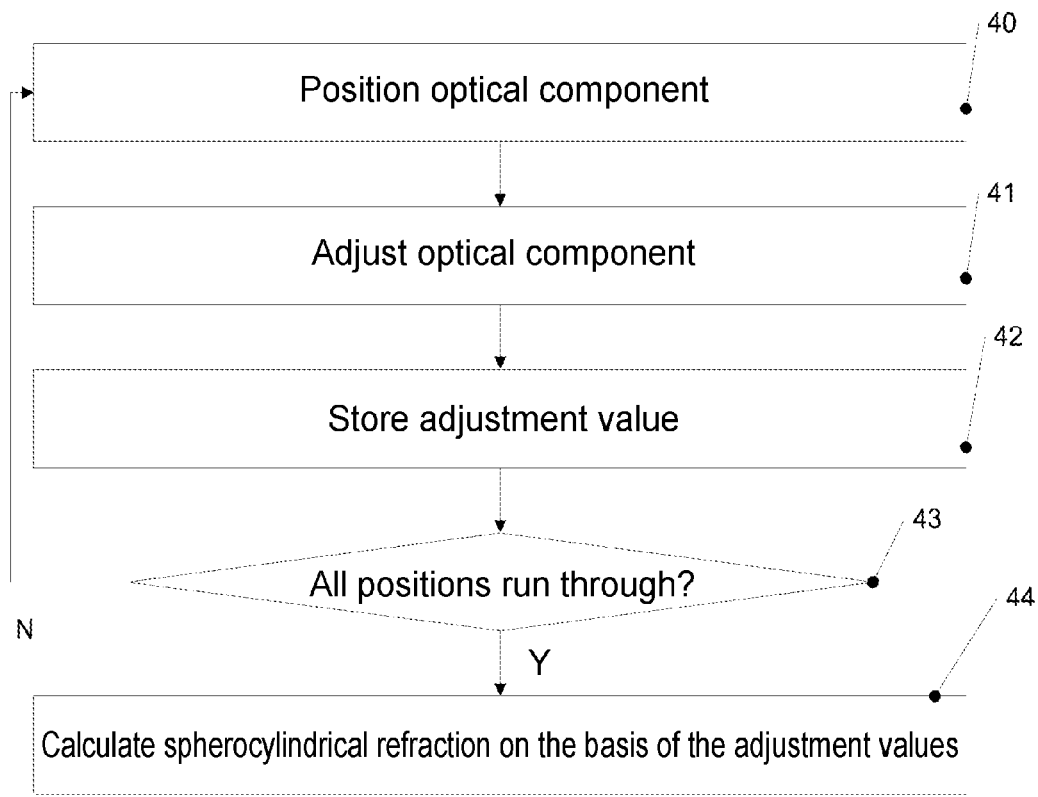
FIG. 4 shows a flowchart of a method according to one exemplary embodiment.

To this end, FIG. 4 illustrates a flowchart for elucidating a first method for determining the spherocylindrical refraction of an eye.

To this end, an optical unit with a typical direction, e.g., the Alvarez lens 20 of FIG. 2, is positioned with a first orientation of the typical direction and optotypes are observed through the optical unit in step 40. The distance between the optical unit and the eye to be examined is typically 12 mm in this case, corresponding to the optimal vertex distance. This distance can be ensured by an implementation as a head-mounted apparatus, as in FIG. 3, or it may be selected accordingly by the user. Here, the vertex distance describes the distance between the front surface of the cornea of the eye and the back surface of the optical area of the optical unit. As a standard, the vertex distance is assumed or set to approximately 12 mm as a distance from the optical unit in the case of subjective refraction since this, on average, represents the most frequent distance when corrective spectacles are worn. If shorter or longer vertex distances are used, the values of the spherocylindrical refraction that are used for a spectacle lens to be manufactured must be corrected in respect of the different vertex distances. This correction can be implemented according to $S2=S1(1+(e2-e1)S1)$. Here, S1 is a first vertex power ascertained at a first vertex distance, from which a second vertex power S2 is calculated at a second vertex distance e2. The vertex power is the reciprocal of the back focus, i.e., the distance of the focus from the vertex of a spectacle lens. Thus, a vertex power ascertained at one vertex distance can be converted to a vertex distance at another vertex power. Here, there usually is a correction of the spherical refractive power only; usually, there is no correction of the cylindrical refractive power and the axis position thereof. In this case, S1 corresponds to the spherical refractive power at the vertex distance e1, from which the spherical refractive power S2 at the vertex distance e2 can be calculated.

In step 41, the optical unit is adjusted to a setting value by means of the refractive power setting device such that the person to be examined can identify the optotypes to the best possible extent (a visual acuity of 1.0 or, typically, at least a visual acuity of 0.8). Here, the optical unit is set in step 41 in such a way that the optical unit is initially set to a setting value corresponding to a maximum positive refractive power. Here, setting to the maximum positive refractive power can be implemented in automated fashion.

Proceeding therefrom, the setting value is modified until the smallest optotypes, at least with the visual acuity of 0.8 at the corresponding distance, are identified for the first time. The corresponding setting value is stored at 42. Here, the visual acuity is the reciprocal of the resolution capability in arc minutes. For a visual acuity of 1.0, the detail of the optotypes to be identified has a size of 1' (arc minute) as seen from the eye. Here, the visual acuity approximately corresponds to the arctan of the ratio of size of the optotype to the distance of the optotype from the eye. In the case of the visual acuity of 0.8, the detail of the optotype to be identified has a size of 1.25'.

As indicated by a step 43, steps 40-42 are repeated a number of times for different orientations of the typical direction of the optical unit until all required positions have been run through. In the exemplary embodiment of FIG. 4, steps 40-42 are run through, in particular, for three different orientations of the typical direction of the optical unit. This is illustrated in FIG. 5.

Figure 5:
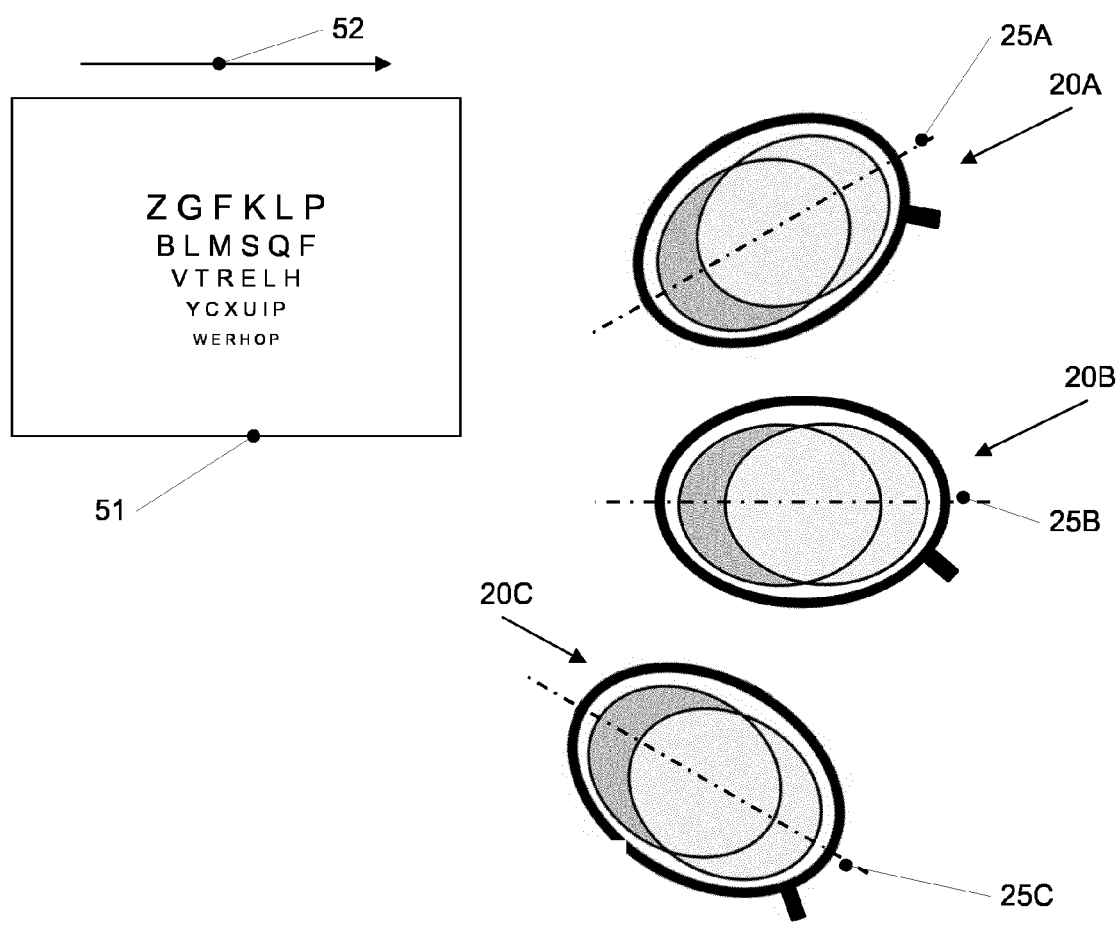
FIG. 5 shows an illustration for explaining the method of FIG. 4.

FIG. 5 shows three different orientations for the Alvarez lens 20 as an example of the optical unit, denoted by 20A, 20B, 20C in FIG. 5. The respective axes 25 that specify the typical direction are denoted by 25A, 25B and 25C. In particular, the axes 25A-25C are at three different angles to a row direction 52 of an eye chart 51. The eye chart 51 displays symbols that become smaller from row to row. Here, the size of the optotypes differs by 0.1 log MAR steps from row to row such that the optotype size is displayed logarithmically according to the Weber-Fechner law. The minimum displayed visual acuity value should be −0.1 log MAR, i.e., correspond to a decimal visual acuity of 1.25. In the case of FIG. 5, the eye chart 51 is simply printed cardboard. Here, the axes 25A-25C are at angles of 0° (axis 25B), +60° (axis 25A) and −60° (axis 25C) in relation to the row direction 52. In general, at least three measurements are carried out in steps 40-42 in the exemplary embodiment of FIG. 4, with the orientations of the typical direction of the optical unit differing from measurement to measurement by approximately 60° in the exemplary embodiment of FIG. 5.

After this has been carried out for all positions of FIG. 5, the spherocylindrical refraction is calculated in step 44 on the basis of the setting values stored at 42. Here, a check is initially carried out as to whether the same setting value was stored at 42 for all orientations of the typical direction. Should this be the case, this means that the examined eye has no astigmatism, i.e., the refractive power of the eye has no cylindrical component. The user is informed accordingly in this case. Since an accurate determination of the sphere is not possible with sufficient accuracy using the recorded setting values, the user may then determine the spherical refractive power of their eye by means of a purely spherical adjustable lens. Alternatively, the cylindrical refractive power of the Alvarez lens 20 can be changed by displacing the lens halves in relation to one another in a direction perpendicular to the axis 25 and the measurement at 42 can be repeated at least for one orientation of the typical direction. Then, the spherical refractive power can be determined from the additional setting value obtained thus and the already available setting values.

Then, parameters A, B and D are calculated as follows on the basis of the various setting values for the orientations of FIG. 5:

$$A = \frac{\text{Refraction } 0°(D) + \text{Refraction} - 60°(D) + \text{Refraction} + 60°(D)}{3} \quad (1)$$

$$B = \frac{2 * \text{Refraction } 0°(D) - \text{Refraction} - 60°(D) + \text{Refraction} + 60°(D)}{3} \quad (2)$$

$$D = \frac{\text{Refraction} - 60°(D) - \text{Refraction} + 60°(D)}{\sqrt{3}} \quad (3)$$

Here, Refraction 0° (D) denotes the set refractive power of the Alvarez lens 20B with the axis position 25B of FIG. 5 in diopter, Refraction +60° (D) denotes the set refractive power of the Alvarez lens 20A with the axis position 25A of FIG. 5 in diopter, and Refraction −60° (D) denotes the set refractive power of the Alvarez lens 20C at the axis position 25C, i.e., the setting value adjusted in step 41 and stored in step 42 in each case. For other angle positions, which do not differ by 60° from one another in each case, Equations (1) to (3) have to be adapted in a manner known per se. By way of example, this is described in the aforementioned publication by Gekeler et al., 1997. Further information items in relation to the aforementioned calculations can also be gathered from Thibos et al., Optometry and Vision Science Vol. 74 no. 6 pages 367-375.

Now, the spherocylindrical refraction of the examined eye can be calculated as follows from these parameters:

$$1. \text{ Sphere} = A + \sqrt{(B^2 + D^2)} \quad (4)$$

$$2. \text{ Cylinder} = -2\sqrt{(B^2 + D^2)} \quad (5)$$

$$3. \text{ Axis} = 0.5 * \arctan\left(\frac{D}{B}\right) \quad (6)$$

The values for sphere, cylinder and axis from Equations (4)-(6) then specify the spherocylindrical refraction in minus cylinder notation, which is usually used in Germany for spectacle lens prescriptions. In the minus cylinder notation, the mathematically smaller principal meridian refractive value is selected for the spherical refractive power (sphere), as a result of which the cylindrical component of the refractive power (cylinder) obtains a negative sign (in this respect, see also H. Goersch, Wörterbuch der Optometrie, 3rd edition, ISBN 978-3-922269-43-4).

If the measurement is carried out at a distance of less than approximately 5 m between eye and eye chart 51 (which, to a good approximation, corresponds to the focusing of the eye at infinity), the sphere (Equation 4) must still be corrected by the magnitude of the distance. Here, the distance in meter must be converted as a reciprocal value in diopter and the obtained spherical correction must be corrected by this value.

More details in respect of these calculations can be gathered from, for example, the aforementioned publication by Gekeler et al.

The cylindrical refractive power of the Alvarez lens 20 is neglected in the aforementioned calculation; this leads to acceptable results in the case of values of less than 0.5 dpt and simplifies the calculation. Otherwise, the cylindrical refractive power of the Alvarez lens 20 can also be included, with the fact that the direction of an overall cylindrical effect of the optical system made of eye and Alvarez lens 20 is determined from the direction and magnitude of the cylindrical refractive power of the Alvarez lens 20 and the axis and the cylindrical refractive power of the eye then also having to be taken into account in the calculation. Thus, it is then possible, for example, to determine the cylindrical refractive power of the eye taking account of the spherical refractive power and cylindrical refractive power of the Alvarez lens.

Then, the result for the examined person is output following the calculation in step 44. Then, the method can be repeated for the respective other eye in order to examine both eyes of the person.

Figure 6:
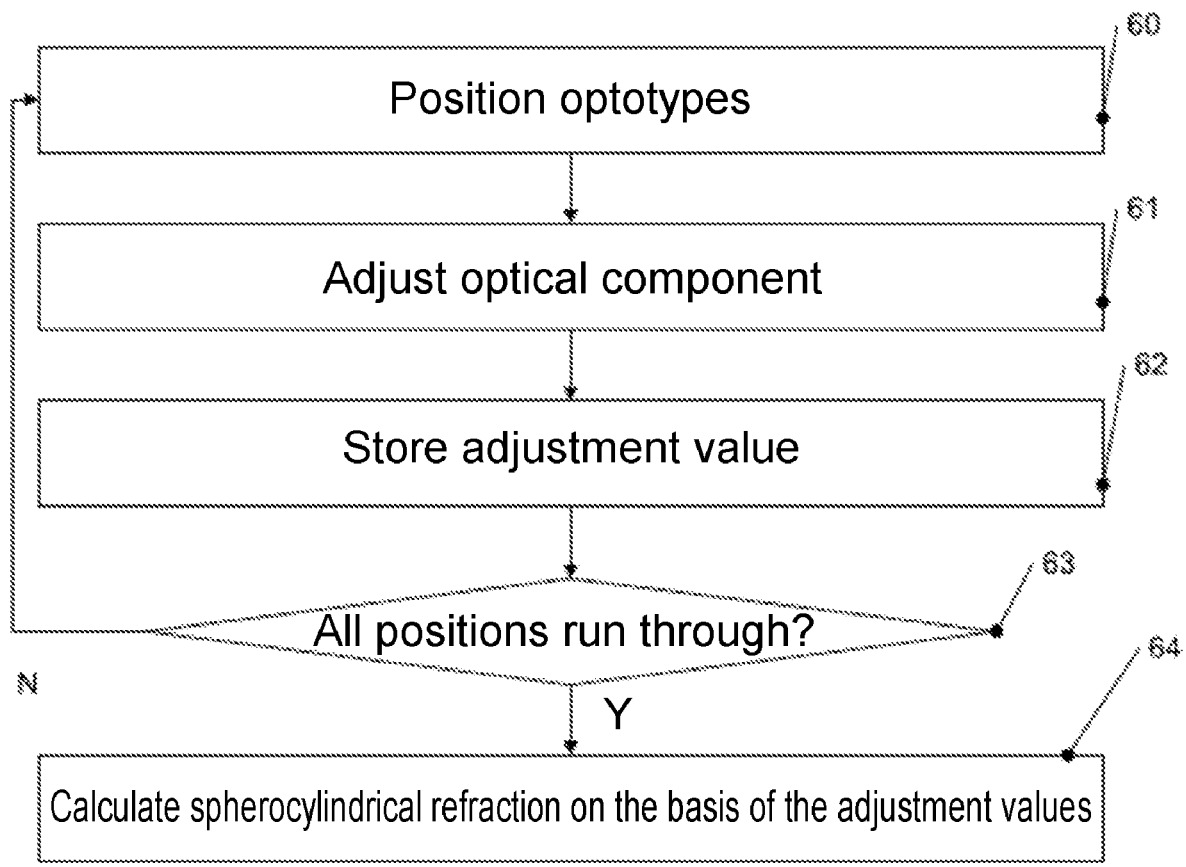
FIG. 6 shows a flowchart of a method according to a further exemplary embodiment.
Figure 7:
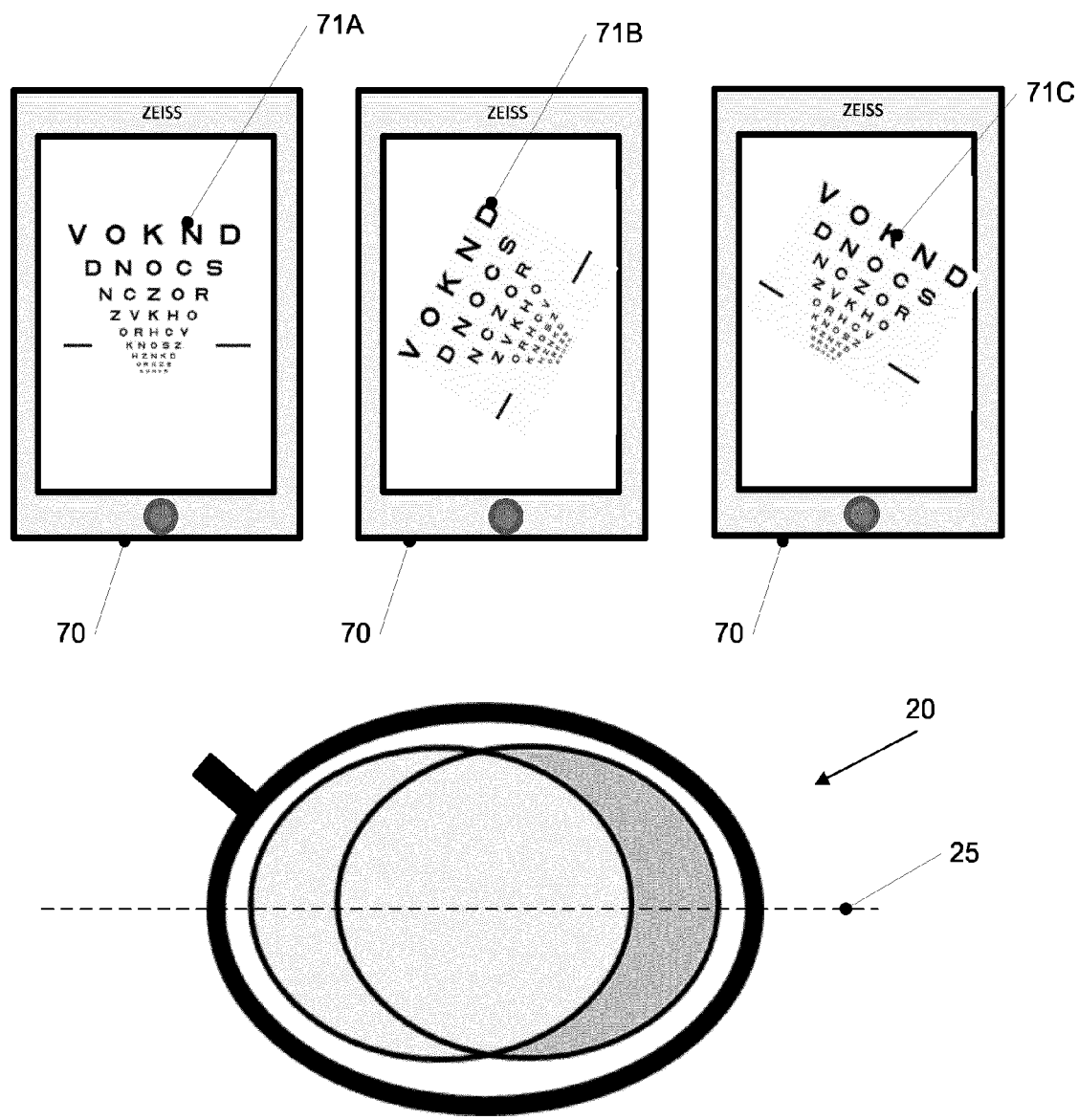
FIG. 7 shows an illustration for elucidating the method of FIG. 6.

Next, an alternative to the method of FIGS. 4 and 5 is presented with reference to FIGS. 6 and 7, in which it is not the orientation of the typical direction of the optical unit but the orientation of the typical direction of the optotypes that is modified.

FIG. 6 shows a flowchart of this method.

In FIG. 6, optotypes whose typical direction is defined by a row direction are presented with a first orientation of this typical direction in a step 60. Then, an optical unit is set in such a way in step 61 that the optotypes are identifiable to the best possible extent. This corresponds to the setting of step 41 in FIG. 4 and can be implemented as described for step 41 in FIG. 4.

In step 62, the corresponding setting value is stored, as already described for step 42 in FIG. 4. As indicated by a step 63, steps 60-62 are run through multiple times, in particular three times, as was also already explained for steps 40-42 in FIG. 4. Here, the optotypes in step 60 are positioned at a different angle position in each passage, i.e., the orientation of the typical direction is changed. The method of FIG. 6 thus differs from the method of FIG. 4 in that the optical unit is not positioned with different orientations of the typical direction like in step 40; instead, the optotypes are positioned with different orientations of the typical direction in step 60. This will now be explained in more detail with reference to FIG. 7.

FIG. 7 illustrates the Alvarez lens 20 of FIG. 2 with the axis 25, with the axis 25 extending in the horizontal direction in FIG. 7. Optotypes with three different orientations of the typical direction are displayed on a display 70 during three iterations of step 60, as denoted by reference signs 71A, 71B and 71C in FIG. 7. Here, in the illustrated example, the display 70 is the display of a tablet computer and is an example of the implementation of the device 12 of FIG. 1.

Here, in the case of the optotypes 71A, a row direction (typical direction) of the optotypes 71A is parallel to the axis 25, which is referred to as 0° position in accordance with the illustration of FIG. 5. In relation thereto, the optotypes 71B are rotated through +60°; the optotypes 71C are rotated through −60°. Thus, three measurements are carried out like in FIG. 5, with the rotation between the measurements being approximately 60° in each case.

In step 64, the spherocylindrical refraction is calculated on the basis of the setting values like in step 44, with use being made of the same Equations (1) to (6) as in step 44.

In the exemplary embodiments illustrated with reference to FIGS. 4-7, problems may arise with the correct setting of the optical unit for persons with astigmatic refractive errors of greater than 1.00 dpt. A modified method, in particular, can be carried out for such persons to be examined, the modified method now being explained with reference to FIGS. 8 and 9. In this method, the refraction determination is performed in the two so-called principal meridians, which have a maximum or minimum refractive value of the eye.

Figure 8:
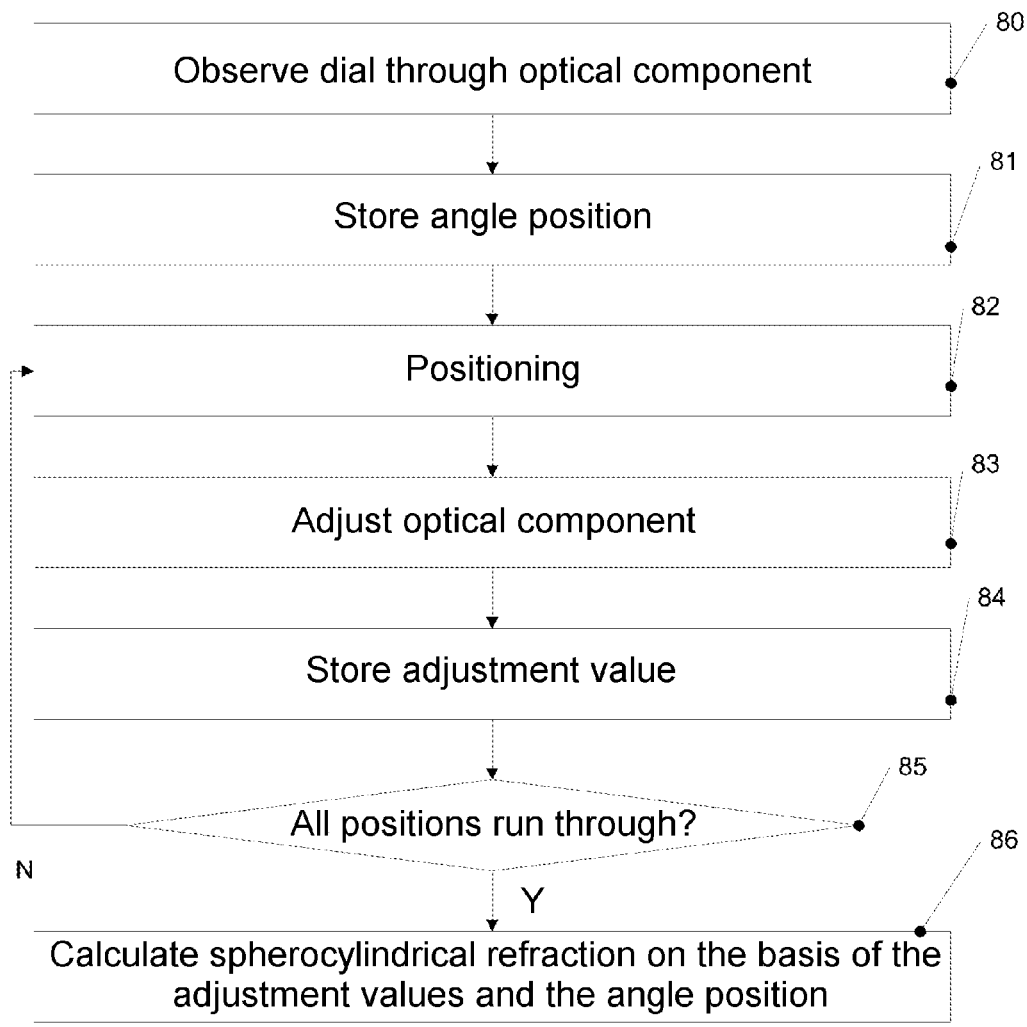
FIG. 8 shows a flowchart of a method according to a further exemplary embodiment.
Figure 9:
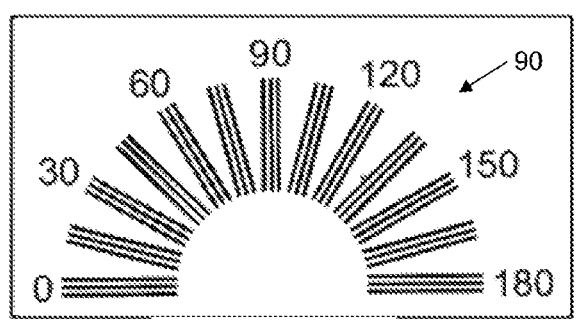
FIG. 9 shows a starburst for use in the method of FIG. 8.

FIG. 8 shows a flowchart of this method. In step 80, a ray circle, in particular the so-called astigmatic dial, is displayed on a display. Such a dial 90 is shown in FIG. 9; it has lines that point in different directions. Moreover, an angle scale is illustrated.

The optical unit, for example the Alvarez lens 20 of FIG. 2, is then set to the maximum positive refractive power. As a result, the eye of the person to be examined is made artificially myopic. Then, the dial of FIG. 9 appears to the person to be very unsharp at some angle positions and less unsharp at other angle positions. The examined person specifies the position at which the dial has the best sharpness; this is equivalent to a maximum perceived blackening at this position. If the entire dial is too unsharp to be able to determine this, the optical unit may also be adjusted until such a distinction of the best sharpness is possible.

Then, this angle position is stored in the computing device 11 of FIG. 1 in step 81 and it represents an information item about an axis position of the examined eye.

This is directly followed by steps 82 to 85, which correspond to steps 40 to 43 in FIG. 4 or steps 60 to 63 in FIG. 6; i.e., the optical unit or the optotypes are positioned with different orientations of their typical direction, the optical unit is set and the respective setting value is stored. However, in contrast to FIG. 4 and FIG. 6, steps 82 to 84 in the exemplary embodiment of FIG. 8 are only implemented for two orientations of the typical direction, namely for an orientation in which the typical direction (axis 25 or row direction 51) corresponds to the angle position determined in step 80 and stored in step 81, and for an orientation rotated through 90° in relation thereto.

By way of example, if the best sharpness is identified in the angle position 150° of FIG. 9, the optotypes are initially displayed on the display 70 of FIG. 7 at an angle of 150° in step 82 or the typical direction of the adjustable optical unit is aligned at an angle of 150° in a manner corresponding to the procedure of FIG. 5. Then, in step 83, the optical unit is initially set to a maximum positive effect and then adjusted until even the smallest optotypes are recognized in focus for the first time. This setting value is then stored in step 84. Then, steps 82 to 84 are repeated, with either the optotypes on the display 70 or the optical unit being rotated through ±90° in comparison with the first iteration. Consequently, the refractive power information for the two principal meridians is available, from which the spherocylindrical refraction can be calculated.

In a numerical example, a refractive power of −3.0 dpt emerges, for example, for the 150° position and a refractive power of −1.0 dpt emerges for the position 60° (rotated from 150° by) 90°. Then, a sphere of −1.0, a cylinder of −2.0 and an axis of 60° or a sphere of −3.0, a cylinder of +2.0 and an axis of 150° emerges as spherocylindrical refraction. Here, the sphere reflects the refractive value belonging to the axis and the cylinder reflects the difference of this refractive value from the refractive value present at 90° to the axis.

The foregoing description of the exemplary embodiments of the disclosure illustrates and describes the present invention. Additionally, the disclosure shows and describes only the exemplary embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

The invention claimed is:

1. A system comprising:
   an optical unit having an adjustable refractive power;
   a refractive power setting device configured to set the refractive power of the optical unit in accordance with a setting value; and
   a computer program stored on a non-transitory storage medium and having a program code which, when executed on a computing device, causes:
      optotypes that are observed through the optical unit to be displayed on a display, and
      a first value, which specifies a spherical refractive power, a second value, which specifies a cylindrical refractive power, and a third value, which specifies an axis position of the cylindrical refractive power, to be calculated on a basis of setting values of the refractive power setting device at different orientations of a typical direction of the optotypes,
wherein the calculation is implemented on the basis of two setting values at two different orientations of the typical direction of the optotypes, and
wherein the calculation is additionally implemented on the basis of an information item about an axis position of an eye.

2. The system as claimed in claim 1, wherein the two setting values at the two different orientations of the typical direction of the optotypes are precisely two setting values.

3. The system as claimed in claim 2, wherein the precisely two different orientations of the typical direction of the optotypes comprise a first orientation along an axis position of the eye and a second orientation, which is rotated through 90° in relation to the axis position of the eye.

4. The system as claimed in claim 1, wherein the program code, when executed on the computing device, causes a dial that is observed through the optical unit to be displayed on the display.

5. The system as claimed in claim 4, wherein the program code is further configured to determine the information item about the axis position of the eye on a basis of an input by a user as to which direction of the dial appears most sharp to the user.

6. A system comprising:
an optical unit with an adjustable refractive power, which has a typical direction of the refractive power;
a refractive power setting device configured to set the refractive power of the optical unit in accordance with a setting value; and
an orientation setting device for setting an orientation of the typical direction of the refractive power,
wherein the system is configured to determine a first value, which specifies a spherical refractive power, a second value, which specifies a cylindrical refractive power, and a third value, which specifies an axis position of the cylindrical refractive power, on the basis of setting values of the refractive power setting device and settings of the orientation of the typical direction of the refractive power, and
wherein the system comprises a computer program stored on a non-transitory storage medium and having a program code which, when executed on a computing device, causes the first value, the second value and the third value to be calculated on the basis of two setting values of the refractive power setting device at two different orientations of the typical direction of the refractive power and on the basis of an information item about an axis position of an eye.

7. The system as claimed in claim 6, wherein the two different orientations of the typical direction of the refractive power are precisely two different orientations of the typical direction of the refractive power.

8. The system as claimed in claim 6, wherein the orientation setting device comprises an alignment sensor configured to measure the orientation of the typical direction of the refractive power.

9. The system as claimed in claim 6, wherein the cylindrical refractive power of the optical unit lies between 0.25 dpt and 0.5 dpt.

10. A system comprising:
an optical unit having an adjustable refractive power, wherein the optical unit has a typical direction of the refractive power;
an orientation setting device configured to set an orientation of the typical direction of the refractive power; and
a refractive power setting device configured to set the refractive power of the optical unit in accordance with a setting value,
wherein the system comprises a computer program stored on a non-transitory storage medium and having a program code which, when executed on a computing device, causes a first value, which specifies a spherical refractive power, a second value, which specifies a cylindrical refractive power, and a third value, which specifies an axis position of the cylindrical refractive power, to be calculated on the basis of at least two setting values of the refractive power setting device at different orientations of the typical direction of the refractive power.

11. The system as claimed in claim 10, wherein the orientation setting device comprises an alignment sensor configured to measure the orientation of the typical direction of the refractive power.

12. The system as claimed in claim 6, wherein the typical direction of the optical unit is defined by an axis position of a cylindrical refractive power of the optical unit, and
wherein the refractive power setting device is configured to set a spherical refractive power of the optical unit in accordance with the setting value.

13. The system as claimed in claim 12, wherein the cylindrical refractive power of the optical unit lies between 0.25 dpt and 0.5 dpt.

14. The system as claimed in claim 6, wherein the program code, when executed on the computing device, causes optotypes that are observed through the optical unit to be displayed on a display.

15. The system as claimed in claim 10, wherein the at least two setting values at different orientations of the typical direction of the refractive power include three setting values at three different orientations of the typical direction of the refractive power.

16. The system as claimed in claim 15, wherein the three different orientations of the typical direction of the refractive power have an angular distance of between 55° and 65° from one another.

17. The system as claimed in claim 6, wherein at least one of the three different orientations of the typical direction of the refractive power has an angular distance of between 55° and 65° from another or the three different orientations of the typical direction of the optotypes have an angular distance of between 55° and 65° from one another.

18. The system as claimed in claim 9, wherein the orientation setting device comprises an alignment sensor configured to measure the orientation of the typical direction of the refractive power.

19. The system as claimed in claim 9, wherein
the program code, when executed on the computing device, causes optotypes that are observed through the optical unit to be displayed on the display.

20. The system as claimed in claim 9, wherein the program code, when executed on the computing device, is configured to cause the computing device to calculate the first value, the second value, and the third value on the basis of the at least two setting values at different orientations of the typical direction of the refractive power.

21. The system as claimed in claim 20, wherein the at least two setting values at different orientations of the typical direction of the refractive power include three setting values at three different orientations of the typical direction of the refractive power.

22. The system as claimed in claim 21, wherein the three different orientations of the typical direction of the refractive power have an angular distance of between 55° and 65° from one another.

23. The system as claimed in claim 1, wherein the optical unit comprises an Alvarez lens or a liquid lens.

24. The system as claimed in claim 1, wherein the refractive power setting device comprises an interface configured to transmit the setting value to the computing device.

25. The system as claimed in claim 1, wherein the system is configured as a head-mounted apparatus, and wherein the head-mounted apparatus comprises the computing device or a receptacle for the computing device.

26. A system comprising:
an optical unit having an adjustable refractive power;
a refractive power setting device configured to set the refractive power of the optical unit in accordance with a setting value; and
a computer program stored on a non-transitory storage device and having a program code which, when executed on a computing device, causes:
optotypes that are observed through the optical unit to be displayed on a display, and
a first value, which specifies a spherical refractive power, a second value, which specifies a cylindrical refractive power, and a third value, which specifies an axis position of the cylindrical refractive power, to be calculated on a basis of three setting values of the refractive power setting device at three different orientations of the typical direction of the optotypes,
wherein the three different orientations of the typical direction of the optotypes have an angular distance of between 55° and 65° from one another.

27. A system for subjective refractometry, comprising:
an optical unit with an adjustable refractive power;
a refractive power setting device configured to set the refractive power of the optical unit in accordance with a setting value; and
a computer program stored on a non-transitory storage device and having a program code which, when executed on a computing device, causes:
optotypes that are observed through the optical unit to be displayed on a display, and
a first value, which specifies a spherical refractive power, a second value, which specifies a cylindrical refractive power, and a third value, which specifies an axis position of the cylindrical refractive power, to be calculated on a basis of three setting values of the refractive power setting device at three different orientations of the typical direction of the optotypes,
wherein the three different orientations of the typical direction of the optotypes have an angular distance of between 55° and 65° from one another.

28. The system as claimed in claim 26, wherein the optotypes have a typical direction, and wherein the program code, when executed on the computing device, causes the optotypes to be displayed successively in time with different orientations of the typical direction of the optotypes.

29. A method for ascertaining a spherocylindrical refraction of an eye of a user, the method comprising:
displaying optotypes at different orientations of a typical direction of the optotypes;
ascertaining respective setting values of an optical unit with an adjustable refractive power at the different orientations of the typical direction of the optotypes; and
calculating a first value, which specifies a spherical refractive power, a second value, which specifies a cylindrical refractive power, and a third value, which specifies an axis position of the cylindrical refractive power, on a basis of setting values at different orientations of the typical direction,
wherein the calculation is implemented on the basis of two setting values at two different orientations of the optotypes, and
wherein the calculation is additionally implemented on the basis of an information item about an axis position of an eye.

30. A method for ascertaining a spherocylindrical refraction of an eye of a user, the method comprising:
displaying optotypes at different orientations of a typical direction of the optotypes;
ascertaining respective setting values of an optical unit with an adjustable refractive power at the different orientations of the typical direction of the optotypes; and
calculating a first value, which specifies a spherical refractive power, a second value, which specifies a cylindrical refractive power, and a third value, which specifies an axis position of the cylindrical refractive power, on a basis of setting values at different orientations of the typical direction,
wherein the calculation is implemented on the basis of two setting values at precisely two different orientations of the optotypes and an information item about an axis position of an eye.

31. The method as claimed in claim 30, wherein the precisely two different orientations of the typical direction of the optotypes comprise a first orientation along the axis position of the eye and a second orientation, which is rotated through 90° in relation to the axis position of the eye.

32. A method for ascertaining a spherocylindrical refraction of an eye of a user, the method comprising:
displaying optotypes at different orientations of a typical direction of the optotypes;
ascertaining respective setting values of an optical unit with an adjustable refractive power at the different orientations of the typical direction of the optotypes; and
calculating a first value, which specifies a spherical refractive power, a second value, which specifies a cylindrical refractive power, and a third value, which specifies an axis position of the cylindrical refractive power, on a basis of setting values at different orientations of the typical direction,
wherein the calculation is implemented on the basis of two setting values at two different orientations of the optotypes,
wherein the calculation is additionally implemented on the basis of an information item about an axis position of an eye, and
wherein the method includes displaying a dial on a display and ascertaining the information item about the axis position on the basis of the dial.

33. A method for ascertaining a spherocylindrical refraction of an eye of a user, the method comprising:
displaying optotypes at different orientations of a typical direction of the optotypes;

ascertaining respective setting values of an optical unit with an adjustable refractive power at the different orientations of the typical direction of the optotypes; and calculating a first value, which specifies a spherical refractive power, a second value, which specifies a cylindrical refractive power, and a third value, which specifies an axis position of the cylindrical refractive power, on a basis of setting values at different orientations of the typical direction, wherein the calculation is implemented on the basis of two setting values at precisely two different orientations of the optotypes and an information item about an axis position of an eye, and wherein the method includes displaying a dial on a display and ascertaining the information item about the axis position on the basis of the dial.

34. The method as claimed in claim 29, wherein the method comprises displaying a dial on a display and ascertaining the information item about the axis position on the basis of the dial.

35. A method for ascertaining a spherocylindrical refraction of an eye of a user, the method comprising:

ascertaining at least two setting values of a refractive power of an optical unit with a typical direction of the refractive power at different orientations of the typical direction of the refractive power; and calculating a first value, which specifies a spherical refractive power, a second value, which specifies a cylindrical refractive power, and a third value, which specifies an axis position of the cylindrical refractive power, on a basis of the at least two setting values, wherein the calculation is implemented on the basis of two setting values at two different orientations of the typical direction of the refractive power, and wherein the calculation is additionally implemented on the basis of an information item about an axis position of an eye.

36. A method for ascertaining a spherocylindrical refraction of an eye of a user, the method comprising:

ascertaining at least two setting values of a refractive power of an optical unit with a typical direction of the refractive power at different orientations of the typical direction of the refractive power; and calculating a first value, which specifies a spherical refractive power, a second value, which specifies a cylindrical refractive power, and a third value, which specifies an axis position of the cylindrical refractive power, on a basis of the at least two setting values, wherein the calculation is implemented on the basis of two setting values at precisely two different orientations of the typical direction of the refractive power and an information item about an axis position of an eye.

* * * * *

UNITED STATES PATENT AND TRADEMARK OFFICE
CERTIFICATE OF CORRECTION

PATENT NO. : 11,129,526 B2
APPLICATION NO. : 16/393987
DATED : September 28, 2021
INVENTOR(S) : Ohlendorf et al.

Page 1 of 1

It is certified that error appears in the above-identified patent and that said Letters Patent is hereby corrected as shown below:

In the Specification

Column 15, Lines 48 to 49, change the numerator of parameter B from "2*Refraction 0° (D) - Refraction -60° (D) + Refraction +60° (D)" to -- 2*Refraction 0° (D) - Refraction -60° (D) - Refraction +60° (D) --.

Signed and Sealed this
Twenty-eighth Day of December, 2021

Drew Hirshfeld
*Performing the Functions and Duties of the
Under Secretary of Commerce for Intellectual Property and
Director of the United States Patent and Trademark Office*